United States Patent [19]

Nicolaou et al.

[11] Patent Number: 5,500,432

[45] Date of Patent: Mar. 19, 1996

[54] INDUCTION AND INHIBITION OF APOPTOSIS

[75] Inventors: K. C. Nicolaou, La Jolla; Andrew Hiatt, San Diego; Wolfgang Wrasidlo, La Jolla, all of Calif.

[73] Assignee: The Scripps Research Institute, La Jolla, Calif.

[21] Appl. No.: 46,626

[22] Filed: Apr. 14, 1993

Related U.S. Application Data

[63] Continuation-in-part of Ser. No. 939,104, Sep. 1, 1992, Pat. No. 5,281,710, which is a continuation-in-part of Ser. No. 886,984, May 21, 1992, Pat. No. 5,276,159, which is a continuation-in-part of Ser. No. 788,225, Nov. 5, 1991, abandoned, which is a continuation-in-part of Ser. No. 734,613, Jul. 23, 1991, abandoned, which is a continuation-in-part of Ser. No. 673,199, Mar. 21, 1991, abandoned, which is a continuation-in-part of Ser. No. 562,269, Aug. 1, 1990, abandoned.

[51] Int. Cl.$^6$ .................................................. A61K 31/44
[52] U.S. Cl. .......................................................... 514/281
[58] Field of Search ................................................ 514/281

[56] References Cited

PUBLICATIONS

Nicolaou et al. Angew. Chem. It. Ed. Eng. (1991), 30, 1032–1036.
Nicolaou et al. J. Am. Chem. Soc. (1992), 114, 8890–8907.
Nicolaou et al. J. Am. Chem. Soc. (1993), 115, 7944–7953.
Nicolaou et al. Angew. Chem. It. Ed. Eng (1989), 28, 1272–1275.
Mair et al. Tet. Letters (1991), 32, 3679–3682.
Nicolaou et al. J. Am. Chem. Soc. (1992), 114, 9279–9282.
Nicolaou et al. Angew. Chem. It. Ed. Eng. (1991), 30, 418–420.
Nicolaou et al. Angew. Chem. It. Ed. Eng. (1991), 30, 1387–1416.

*Primary Examiner*—Kimberly Jordan
*Attorney, Agent, or Firm*—Donald G. Lewis

[57] ABSTRACT

A method for inducing apoptosis in target cells employs designed enediynes which are triggered to become chemically reactive when bound to target cells. Conversely, a method for inhibiting the induction of apoptosis employs compounds which compete with the above compounds which induce apoptosis, but which are chemically unreactive with respect to the target cells.

4 Claims, 2 Drawing Sheets

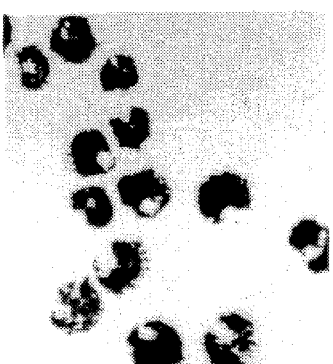
FIG. IC
FIG. IB
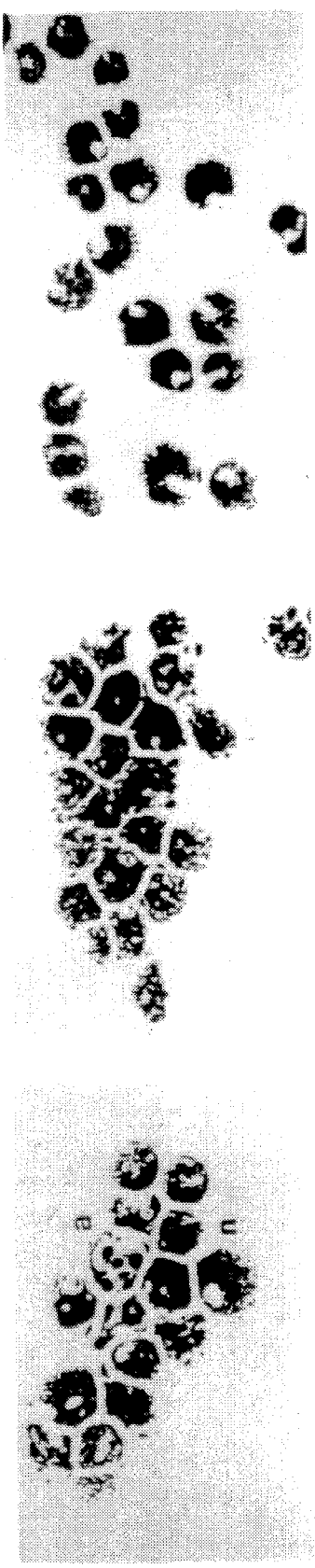
FIG. IA
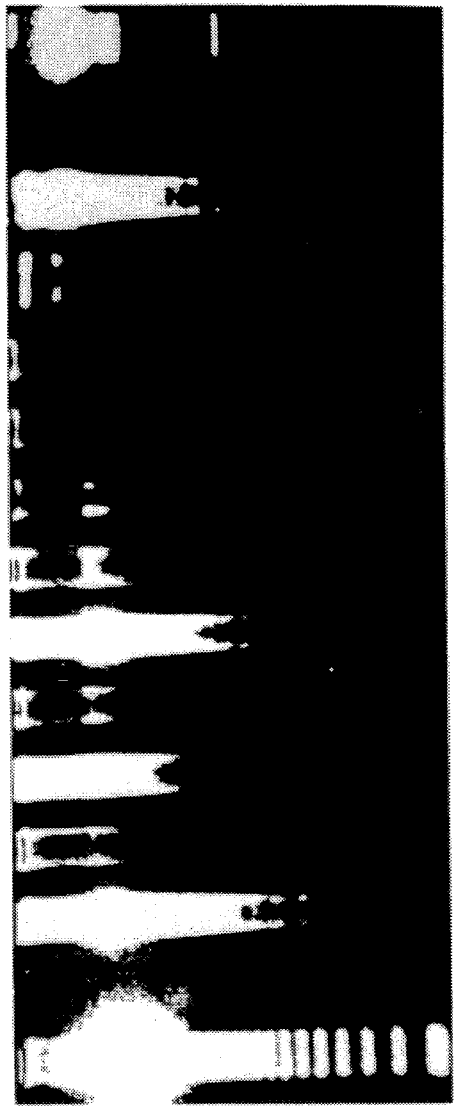
FIG. IE
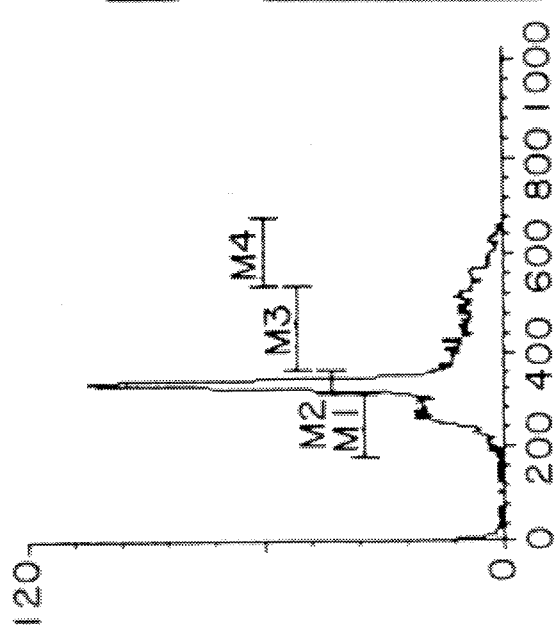
FIG. ID

INDUCTION AND INHIBITION OF APOPTOSIS

GOVERNMENT RIGHTS

This invention was made with government support under Grant No. GM 46446 awarded by the National Institutes of Health. The U.S. government has certain rights in the invention.

CROSS-REFERENCE TO RELATED APPLICATIONS

The present application is a continuation-in-part of U.S. patent application Ser. No. 07/939,104, filed Sep. 1, 1992, now U.S. Pat. No. 5,281,710, that is a continuation-in-part of U.S. patent application Ser. No. 07/886,984, filed May 21, 1992, now U.S. Pat. No. 5,276,159, that is a continuation-in-part of U.S. patent applicati 07/788,225, filed Nov. 5, 1991, now abandoned, that is a continuation-in-part of U.S. patent application Ser. No. 07/734,613, filed Jul. 23, 1991, now abandoned, that is a continuation-in-part of U.S. patent application Ser. No. 07/673,199, filed Mar. 21, 1991, now abandoned, that is a continuation-in-part of U.S. patent application Ser. No. 07/562,269, filed Aug. 1, 1990, now abandoned, whose disclosures are incorporated herein by reference.

FIELD OF THE INVENTION

The invention relates to methods for controlling apoptosis. More particularly, the invention relates to the use of designed enediynes for inducing and inhibiting apoptosis.

BACKGROUND OF THE INVENTION

Apoptosis is an active process whereby selected cells undergo drastic morphological changes. (Kerr et al., 1972, Br. J. Cancer, 26:239–245.) The goal of apoptosis is to attain an orderly disintegration of cells into structures suitable for phagocytosis. (Duval et al., 1985, Immunology, 56:351–358; Savill et al., 1989, J. Clin. Invest., 83:865–875; and Savill et al., 1989, J. Clin. Invest., 84:1518–1527.) The orderly disintegration of cells includes chromatin condensation and degradation of genomic DNA into nucleosomal fragments and cellular fission to form apoptotic bodies. The precise molecular mechanism of apoptosis is uncharacterized.

Apoptosis is known to be involved in developmental and tissue specific processes which require removal of cell populations. (Hamburger et al., 1982, Neurosci. Comment., 1:39–44 and Lesser et al. Biochimica et Biophysica Acta, 308:426–437.) Apoptosis is also known to be involved in the immunological process of cell selection. (Teh et al., 1988, Nature, 335:229–233; Shi et al., 1989, Nature, 339:625–626; and Nunz et al., 1991, Nature, 353:71–74.) The colonic mucosa is known to undergo apoptosis as a result of an invasion by Shigella (Zychlinsky et al., 1992, Nature, 358: 167–169.) During HIV infection, virally induced T cell death has been shown to follow an apoptotic pathway. (Terai et al., 1991, J. Clin. Invest., 87:1710–1715). Similarly, during tumor regression, tumor cell death has been shown to follow an apoptotic pathway. (Szende et al., 1990, Cancer Research, 50:3716–3721; Trauth et al., 1989, Science, 243:301–304; and Kyprianou et al., 1991, Cancer Res., 52:162–166.)

Control of apoptosis has been shown to be useful with respect to specific cells having crucial relevance to developmental biology. (Ellis et al., 1991, Annu. Rev. Cell. Biol., 7:663–398 and Raff, 1992, Nature, 356:397–400). Additionally, it would be useful to control apoptosis with respect to treatments involving viral and bacterial pathogens. (Meyaard et al., 1992, Science, 257:217–220 and Zychlinsky et al., supra.) Cancer chemotherapy could also be enhanced by the controlling apoptotic pathways. (Wyllie et al., 1985, Anticancer Res., 5:131–136.)

The chemical induction of apoptosis is target cell dependent. Glucocorticoids, such as dexamethasone, have been shown to induce apoptosis in thymocytes. (Telford et al., 1991, Cell Prolif., 24: 447.) Cycloheximide, a known inhibitor of protein synthesis and actinomycin D, a known inhibitor of mRNA transcription, have also been shown to be powerful inducers of apoptosis in many cell lines, including Molt-4. (Bansal et al., 1991, FASEB J., 5:211–216; Waring et al., 1990, J. Biol. Chem., 265:14476–14482; Uesawa et al., 1991, Biochemistry, 30:9242–9246; and Dedon et al., 1992, Biochemistry, 31:1909–1917.) Other inducers of apoptosis include UV irradiation, camptothecin, aphidocholin, cisplatin, vincristine, and phorbol myristate acetate plus ionomycin. (Cotter et al. 1992, Cancer Research, 52:9979–1005.)

The inhibition of apoptosis is also target cell dependent. In addition to being classified as apoptosis inducers, actinomycin D and cyloheximide have also been classified as powerful inhibitors of apoptosis in many cell lines, including Molt-4. (Telford, supra.) Other apoptosis inhibitors include various endonuclease inhibitors, e.g. $Zn^{2+}$ (Cohen et al., 1984, J. Immunol., 132:38–42 and Duke et al., 1983, Proc. Natl. Acad. Sci., U.S.A., 80:6361–6365) and aurintricarboxylic acid. (Telford, supra)

Inhibition of apoptotic deletion of autoreactive T-cell clones may be achieved by treatment with immunosuppressant cyclosporin A. In this case, the inhibition of apoptosis may lead to autoimmune disease. Other special inhibitors of apoptosis, including various steroids and interleukins, are reviewed by Ellis et al., 1991, Annu. Rev. Cell. Biol., 7:663–398.

The latter stage of apoptosis, i.e. the induction of fission events leading to the formation of apoptosis bodies, may be inhibited by the use of microfilament-disrupting agents such as cytochalasin B and staurosporin. (Cotter et al., 1992, Cancer Res., 52:997–1005.)

Agents which inhibit the expression of the oncogene cMyc (Shi et al., 1992, Science, 257:212–215) or which cause the over expression of proto-oncogene bcl-2 (Jacobson et al., 1993, Nature, 361:365–369) can inhibit the induction of apoptosis.

What was needed was a method for inducing apoptosis which employs a chemically reactive compound specifically activatable for inducing apoptosis by binding target cells. What was also needed was an inhibitor of such specific chemically reactive inducers of apoptosis.

SUMMARY

The naturally occurring enediyne antibiotics are a unique class of antitumor drugs that combine reactive enediynes with additional structural features conferring affinity for DNA. Dynemicin A, in which an enediyne core is attached to an anthraquinone group capable of DNA intercalation, readily cleaves double stranded DNA. This activity is thought to be the basis of its potent antitumor cytotoxicity.

To investigate cell specific mechanisms of cytotoxicity in the absence of DNA affinity, we have synthesized a variety of dynemicin-like enediynes which lack the anthraquinone moiety. We have found that the cytotoxicity of these compounds is dependent on their chemical instability and their enantiomeric form. Their selective toxicity results from a potent induction of apoptosis primarily in human leukemic cells. A group of synthetic enediynes were designed to be highly stable. These compounds were found to inhibit apoptotic cell death. This inhibition was observed in competition with the chemically unstable enediynes, including dynemicin and calicheamicin. The stable synthetic enediynes could also block the apoptotic morphology induced by unrelated cytotoxic agents such as cycloheximide, actinomycin D, and ultraviolet light. The results suggest that the cellular target(s) of synthetic enediynes may play a central role in regulating programmed cell death; a specific receptor-ligand interaction is proposed.

Induction of Apoptosis

The invention includes a method for inducing apoptosis within a target cell. The induction method comprising a step for providing a inducing compound having an activity for inducing apoptosis within the target cell and a step for contacting the target cell with the inducing compound under conditions for inducing apoptosis therein. The inducing compound has a fused ring structure and a binding specificity for proteinaceous material within the target cell. The inducing compound also has an enediyne structure attached to the fused ring structure, the enediyne being subject upon triggering to a Bergman reaction for abstracting protons from bound proteinaceous material. The inducing compound also has a trigger structure attached to the fused ring structure activatable at intracellular (alkaline) pH for triggering the enediyne. When the target cell is contacted with the inducing compound, the inducing compound enters the target cell and binds to proteinaceous components therein, activating the trigger. Activation of the trigger initiates the Bergman reaction within the enediyne structure and causes the inducing compound to abstract a proton from the proteinaceous material, thereby inducing apoptosis.

A preferred inducing compound is illustrated below as compound 1, viz.:

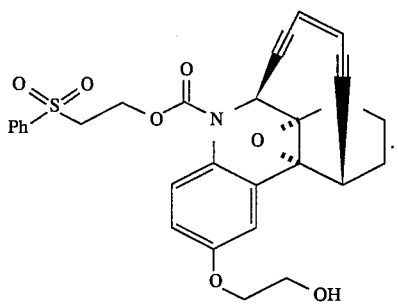

Induction of Apoptosis

The invention also includes a method for inhibiting apoptosis within a target cell. The method comprising the steps of providing an inhibiting compound having an activity for inhibiting the induction of apoptosis by compound 1 (supra) and then contacting the target cell with the inhibiting compound under conditions for inhibiting apoptosis therein. The inducing compound has a fused ring structure and a binding specificity for proteinaceous material within the target cell. The binding specificity of the inhibiting compound is competitive with a binding specificity of compound 1 with respect to a proteinaceous component within the target cell. When the target cell is contacted with the inhibiting compound, the inhibiting compound enters the target cell and binds to a proteinaceous component therein and thereby inhibits apoptosis.

A preferred inhibiting compound is illustrated below as compound 2, viz.:

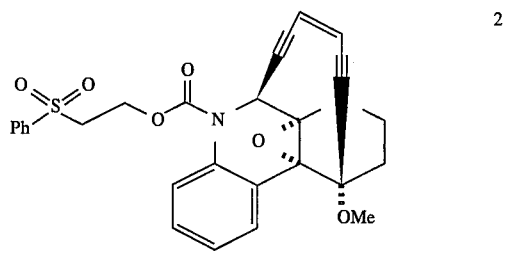

BRIEF DESCRIPTION OF THE DRAWINGS

FIG. 1. Apoptosis and nucleosomal fragments induced by enediynes. Cells were exposed to enediyne for 4 hours after which they were visualized by staining or DNA was extracted or flow cytometry was performed as described in Methods. (A) Molt-4 cells after 4 hours of $10^{-7}$ M enediyne 1 (a=apoptotic, n=normal); (B) Molt-4 cells after 4 hours of $10^{-7}$ M enediyne 1+$10^{-4}$ M enediyne 2; (C) Norma Molt-4 cells; (D) Distribution of cells after enediyne 1 treatment: M1 (apoptotic), 23%; M2 (G0/G1), 43%; M3 (S), 27%; M4 (G2/M), 7%. (E) DNA extracted from $10^6$ Molt-4 cells after four hours of exposure to the following conditions: Lane 1, 1 μg/mL actinomycin,; lane 2, 1 μg/mL actinomycin+$10^{-4}$ M enediyne 2; lane 3, 100 μg/mL cycloheximide; lane 4, 100 μg/mL cycloheximide+$10^{-4}$ M enediyne 2; lane 5, $10^{-7}$ M enediyne 1; lane 6, $10^{-7}$ M enediyne 1+$10^{-4}$ M enediyne 2; lane 7, $10^{-7}$ M enediyne 1+500 μM $ZnCl_2$; lane 8, $10^{-4}$ enediyne 2; lane 9, no additions; lane 10, ultraviolet light (302 nm, 15 minutes)+$10^{-4}$ M enediyne 2; lane 11, ultraviolet light, 15 minutes. The lanes at each end of the gel are molecular weight standards.

DETAILED DESCRIPTION

Materials and Methods

Figure 2:
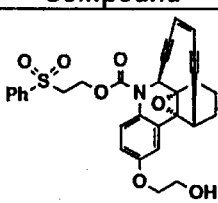
FIG. 2. Chemical instability and biological activity of enediyne structural analogs. The inherent stability of various enediynes was measured by HPLC using the reaction conditions decribed in Methods. The cytotoxicity against Molt-4 cells was measured after three days of exposure to serial dilutions of $10^{-4}$ M of each compound. Apoptosis was quantified by microscopic inspection of cells prepared as described in Methods. A, the $IC_{50}$ (M) values for each enediyne determined using a starting concentration of $10^{-4}$ M as described in Methods; B, the chemical instability index at pH 11; C, the chemical instability at pH 10.5; D, the apoptotic index using $10^{-7}$ M enediyne; E, the apoptotic index using $10^{-6}$ M enediyne.

Drugs and chemicals. Dynemicin A was supplied by Dr. M. Konishi, Bristol-Meyers-Squibb, Japan and calicheamicin $_{\gamma 1}{}^I$ was donated by Drs. G. Ellestad and D. Borders of Lederie Laboratories, U.S.A. Actinomycin D and cycloheximide were from Sigma (St. Louis, Mo.). The synthesis of enediynes 1 and 2 has previously been described (20) as have enediynes 3, 4, 5, 8, 9 (30,31) and enediynes 6 and 7 (32).

Cells and culture conditions. Molt-4 and SK-Mel-28 cell lines were obtained from American Type Culture Collection. Viability assays were performed in microtiter plates using the XTT vital staining method (33). To visualize the apoptotic morphology cells were attached to glass slides by low speed centrifugation and stained with Diff-Quik (Baxter Healthcare Corp., Miami, Fla.). The apoptotic index is the percentage of cells that display the apoptotic morphology. This value was determined in three separate assays for each drug where a minimum of 300 cells were visually scored by microscopy at 50X magnification per assay.

DNA extraction and flow cytometry. DNA extractions were from $10^6$ Molt-4 cells using 10 mM Tris-Cl, 1 mM EDTA, pH 8.0 (TE) containing 0.2% Triton-X-100. DNA was precipitated from the lysate by the addition of 1/10th volume 5 M sodium acetate, pH 5.0 and 3 volumes 95% ethanol. After centrifugation the DNA pellet was resuspended in 25 μL TE containing 1 Mg/mL RNAse A, incubated for 10 min. at 60° followed by agarose gel electrophoresis in Tris-borate buffer.

Flow cytometry was performed on $10^6$ cells using a FACScan cell sorter (Becton-Dickinson, Mountain View, Calif.).

Chemical stability of enediynes. The chemical stability was measured by incubating enediyne in 1 mM ATP, 200 mM phosphate using DMSO to vary the pH to either 10.5 or 11. Reactions were done in a total volume of 20 μL for 10 minutes and were immediately analyzed by HPLC. The percentage of enediyne remaining after the reaction, was used as the parameter of instability where 100 indicates a complete loss of enediyne and zero is a completely stable enediyne.

RESULTS

Apoptotic Cell Death Induced by Enediyne 1

Although synthetic enediynes are capable of DNA cleavage (20), the concentrations required for this activity are far in excess of the physiologically relevant levels. Enediyne 1 kills Molt-4 cells at $10^{-14}$ M however the concentrations required to cleave supercoiled DNA were found to be in the range of $10^{-3}$ M (20). It is well established that dynemicin and calicheamicin can cleave plasmid DNAs at $10^{-5}$ and $10^{-8}$ M respectively. Our cytotoxicity results suggested that enediyne 1, and possibly other enediynes, may accumulate in cells due to an affinity for a target site other than DNA. We found that a 20 minute exposure of Molt-4 cells to $10^{-7}$ M enediyne 1, followed by low speed centrifugation and resuspension in medium without drug, is sufficient for nearly complete cell killing after 22 hours (Table 1). This suggested that enediyne 1 was taken up rapidly by Molt-4 cells and that a program of cell death was being initiated by the pulse.

Examination of cell morphology after 4 hour exposure of Molt-4 cells to $10^{-7}$ M enediyne 1 revealed the typical characteristics of apoptotic cell death (FIG. 1A) compared to normal Molt-4 cells (FIG. 1C). An aggregation of chromatin into a compact granular mass as well as the indentation of the nuclear surface was observed in 20 to 40% of the cells. Subsequently, fragmentation of the nucleus occurred as well as disintegration of the affected cells into apoptotic bodies. The remaining 60–80% of the cells appear to be completely unaffected at this time interval. Flow cytometry analysis of Molt-4 cells at 4 hours of exposure to enediyne 1 corroborated the morphological observations (FIG. 1D).

Apoptotic cell death is also induced at lower concentrations of enediyne 1, however the timing is proportionally delayed. At $10^{-10}$ M enediyne 1, the apoptotic morphology is observed in ~30% of cells after 24 hours. Exposure of SK-Mel 28 melanoma cells to the same concentrations of enediyne 1 at any time interval up to 24 hours did not result in any morphological abnormalities.

TABLE 1

Percent viability of Molt-4 cells after a 20 minute pulse of enediyne 1.

| Time of exposure (h) | Enediyne pulse (M) | | | | |
|---|---|---|---|---|---|
| | control | $10^{-10}$ | $10^{-9}$ | $10^{-8}$ | $10^{-7}$ |
| 1 | 90 | 90 | 90 | 90 | 90 |
| 4 | 87 | 83 | 83 | 83 | 50 |
| 8 | 84 | 75 | 68 | 40 | 22 |
| 22 | 81 | 71 | 57 | 12 | 4 |

$5 \times 10^6$ Molt-4 cells were incubated with varying concentrations of enediyne 1 for 20 minutes followed by low speed centrifugation and resuspension in fresh medium containing no enediyne. Serial dilutions were performed to estimate cell viability at various times using the XTT vital staining method as described in Methods. Data is expressed as the percent of total cells that were viable.

DNA isolated from Molt-4 cells ($10^6$) after 4 hours of exposure to $10^{-7}$ M enediyne 1 clearly demonstrated the characteristic pattern of DNA degradation into nucleosomal fragments (FIG. 1E)(36). In all cases where apoptotic cell death was apparent, we observed nucleosomal fragments.

As has previously been reported in a variety of cell lines, addition of $ZnCl_2$ during induction of apoptosis can inhibit the process and may result in higher levels of cell viability; 0.5 mM $ZnCl_2$ added to Molt-4 cells with $10^{-7}$ M enediyne 1 inhibited both the nucleosome ladder (FIG. 1E) as well as all of the morphological characteristics of apoptosis.

Structural Requirements for Synthetic Enediyne Cytotoxicity

Although enediyne 1 is extremely cytotoxic to Molt-4 cells, a variety of other enediynes that are very similar have reduced cytotoxic capacities. In order to determine the structural requirements of this effect, we quantified both the chemical stability and the apoptotic index of a variety of synthetic enediyne analogs. With the exception of enantiomers of structure 9, the compounds shown in FIG. 2 are not enantiomerically pure. The scheme in FIG. 2 (bottom) depicts a possible rearrangement intermediate resulting from nucleophilic attack (Nu) and chemical instability of the synthetic enediynes.

Chemical instability was defined as the percent enediyne reacting, resulting from exposure of the compound to standardized conditions at elevated pH in vitro (it is assumed that, to a first approximation, instability reflects the ability of each compound to generate radicals (as illustrated in FIG. 2, bottom) except for compound 2, the free amine of which is rather stable under these conditions). After a 10 minute exposure to pH 10.5 or 11, reaction products were quantified by HPLC. The ratio of peak areas of the enediyne before and after the reaction was used as the index of chemical stability. The apoptotic index is the percentage of apoptotic cells after exposure of the Molt-4 line to $10^{-7}$ or $10^{-6}$ M enediyne for 4 hours. These values were compared to the cytotoxicity as measured by dye exclusion assays.

Various strategies were used to modulate the chemical stability of these enediynes. A key element in the generation of benzenoid radicals is the ability of the enediyne ring to collapse due to the unlocking mechanism involving opening of the epoxide ring by electron donation. Electron withdrawing groups at the indicated bridgehead position, such as methoxy (enediyne 2), incapacitate the molecule from entering the Bergman rearrangement (FIG. 2, bottom). Enediyne 2 is not cytotoxic at $10^{-6}$ M nor does it induce apoptosis at that concentration.

β-Elimination involving the phenyl sulfone carbamate attached to the ring nitrogen is required for triggering the cycloaromatization of some of these enediynes leading to benzenoid diradicals (compounds 6 and 7 do not degrade under these conditions, whereas compound 8 suffers a different type of activation involving ester hydrolysis). Chemical modifications of the trigger would be expected to modulate the reactivity and cytotoxicity of the enediyne. In addition, the ability of any particular cell line to activate the trigger may be an important factor determining the cell type specificity of these compounds. Methylation of this moiety at the α-position (enediynes 3, 4, 5) modulates both the chemical stability and cytotoxicity. The mechanism of this effect is not clear. The inability of the molecule to undergo a β-elimination in the case of the thiophenyl carbamate (enediyne 6) or the phenyl sulfoxide carbamate (enediyne 7) completely devoids the molecule from its ability to cause apoptosis and diminishes the cytotoxicity by a factor of $10^8$.

An alternate triggering mechanism involving a t-BuCO2-group attached to the ring backbone (enediyne 8) suggests additional possibilities for modulating the reactivity of these compounds. The results demonstrate that chemical instability of these compounds is a prerequisite for induction of apoptosis and cytotoxicity. This suggests that Bergman cycloaromatization may be the primary mechanism of this cytotoxicity since structures which cannot undergo chemical rearrangement are generally not cytotoxic below $10^{-6}$ M nor do they induce apoptosis.

In addition to the contribution of chemical instability, it is apparent that other structural determinants are contributing to apoptosis and cytotoxicity. The enantiomeric enediynes (−)-9 and (+)-9 readily undergo the Bergman rearrangement reaction in vitro (30,31). Enediyne (−)-9, however, is $10^6$-fold less cytotoxic and also has a significantly lower apoptotic index than (+)-9. The differential cytotoxicity of these stereoisomers suggests that cellular factors which can distinguish enantiomeric forms are mediating their biological effects.

Inhibition of Cytotoxicity and Apoptotic Morphology by Stable Enediynes

To further define how various enediynes may interact with cellular factors to produce cytotoxic effects, we performed competition experiments using enediynes of relatively low cytotoxicity such as compound 2. The experiments were designed to determine if enediynes with low chemical reactivity could block the cytotoxic effects of enediynes with high chemical reactivity. Molt-4 cells were preincubated at an initial concentration of $10^{-4}$ M enediyne 2 for 1 hour. The medium was then made $10^{-7}$ M in enediyne 1 followed by serial dilution to determine the $IC_{50}$. These dilutions were compared to the cytotoxic drug alone at the equivalent initial concentration. The results (Table 2 and FIG. 1E) clearly demonstrate a reduction in the cytotoxicity of enediyne 1 when enediyne 2 is present. Similar experiments were performed in which the naturally occurring enediynes dynemicin and calicheamicin were used to initiate apoptosis. In each case, the cytotoxicity was reduced by a factor of $10^2$–$10^4$.

The reduction in cytotoxicity was also reflected in an absence of the apoptotic morphology of the cells (FIG. 1B). This was quantified by assigning an apoptotic index to the cell population (Table 2). In these assays, Molt-4 cells ($10^5$/mL) were preincubated with $10^{-4}$ M enediyne 2 for 1 hour followed by $10^{-7}$ M enediyne 1, calicheamicin, or dynemicin for 4 hours. In this time frame, the enediynes alone produce a classic apoptotic morphology in 20–40% of the cells. None of the cytotoxic enediynes produce an apoptotic cell morphology in combination with enediyne 2 (FIG. 1B).

To extend these observations, we co-incubated enediyne 2 with initiators of apoptosis which do not contain enediyne functional groups as well as with non-chemical initiators of apoptosis. In many cell lines, including Molt-4, actinomycin D and cycloheximide are powerful inducers of apoptosis. At concentrations of 1 and 100 μg/mL respectively, apoptosis was observed in ~30% of the cells after 4 hours. In each case, no apoptosis was observed at this time interval when enediyne 2 was present at $10^{-4}$ M (Table 2). Exposure of many cell lines to UV light frequently results in extensive apoptosis. Using 302 nm UV light, apoptosis was observed in nearly all Molt-4 cells. Addition of enediyne 2 immediately after

TABLE 2

Inhibition of cytotoxicity and apoptosis in Molt-4 cells by enediyne 2.

| Additions | Percent apoptotic cells | Ladder | IC50 (M) |
|---|---|---|---|
| no additions | 0 | no | — |
| $10^{-4}$ M enediyne 2 | 1 | no | $5 \times 10^{-5}$ |
| $10^{-7}$ M enediyne 1 | 40 | yes | $1 \times 10^{-12}$ |
| $10^{-7}$ M enediyne 1 + 2 | 2 | no | $6 \times 10^{-7}$ |
| $10^{-7}$ M calicheamicin | 43 | yes | $3 \times 10^{-12}$ |
| $10^{-7}$ M calicheamicin + 2 | 1 | no | $2 \times 10^{-8}$ |
| $10^{-7}$ dynemicin | 36 | yes | $4 \times 10^{-11}$ |
| $10^{-7}$ dynemicin + 2 | 1 | no | $5 \times 10^{-9}$ |
| 100 μg/ml cycloheximide | 20 | yes | $2 \times 10^{-7}$ |

TABLE 2-continued

Inhibition of cytotoxicity and apoptosis in Molt-4 cells by enediyne 2.

| Additions | Percent apoptotic cells | Ladder | IC50 (M) |
|---|---|---|---|
| 100 µg/ml cycloheximide + 2 | 2 | no | $5 \times 10^{-7}$ |
| 1 µg/mL actinomycin D | 37 | yes | $3 \times 10^{-8}$ |
| 1 µg/mL actinomycin D + 2 | 2 | no | $4 \times 10^{-8}$ |
| 15 min. UV irradiation | 85 (10% necrosis) | yes | — |
| UV irradiation + 2 | necrosis | no | — |

In each case, the initial starting concentration of cytotoxic drug was $10^{-7}$ M and the initial starting concentration of enediyne 2 was $10^{-4}$ M. Incubation of cells under the various conditions to determine cytotoxicity was for 3 days at a starting concentration of $10^5$ cells/mL. The IC50 molarity refers to the molarity of the cytotoxic drug and was measured using XTT staining as described in Methods.
"Ladder" refers to the presence or absence of a nucleosomal ladder derived from DNA extracted from $10^6$ Molt-4 cells after the 4 hour exposure to drugs or UV.

the UV treatment appeared to subvert the apoptotic pathway into necrosis since 75% of the cells were fully lysed. Of the remaining intact cells, about half had condensed nuclei and half appeared unaffected. Although the cytotoxicity of these treatments is not reduced by the presence of enediyne 2, it is apparent from both the morphological appearance of the cells and from the absence of a nucleosomal ladder (FIG. 1E), that an apoptotic program is not the mechanism of cell death. Similar results were obtained using the stable enediyne 7 as in inhibitor of apoptosis.

DISCUSSION

Calicheamicin and dynemicin, as well as other naturally occurring enediynes are potent antitumor antibiotics which are thought to be cytotoxic due to radical generation occurring at the phosphate backbone of nuclear DNA. Calicheamicin in particular has received considerable attention because its plasmid DNA cleavage has been shown to be sequence selective. If indeed the cytotoxicity of calicheamicin is due to DNA damage, our results demonstrate that this damage is not sufficient to commit Molt-4 cells to a cell death pathway.

We have found that all of the characteristics of apoptotic morphology induced by a variety of initiators are prevented when Molt-4 cells are exposed to stable synthetic enediynes. The increased viability of these cells when stable enediynes are co-incubated with chemically unstable enediynes demonstrates that the stable enediynes are functional at low concentrations, in the range of $10^{-9}$ to $10^{-11}$ M. The results suggest that these enediyne target sites control the ability of Molt-4 cells to undergo apoptotic cell death but do not in all cases affect cell viability. Whereas the stable enediynes clearly control the morphology of cell death, they do not result in increased viability when cycloheximide or actinomycin D are used to initiate cell death. In the case of UV light, cell death clearly occurs by necrosis in the presence of stable enediynes suggesting that necrosis may be an alternate program of cell death when apoptosis is blocked.

The enantiomer specificity of enediyne cytotoxicity as well as the high cell specificity at sub-nanomolar concentrations is strongly suggestive of a protein-mediated mechanism of action. Candidate mechanisms of enediyne action would have to include classic receptor-ligand interactions, such as the steroid hormone receptors, although numerous other models are consistent with the results. Direct measurement of cellular uptake and ligand binding in cell extracts will be necessary to define these mediating events. The ability of the chemically stable enediyne 2 to prevent apoptosis in the absence of a dependence on RNA or protein synthesis suggests an interaction with a pre-existing population of cellular factors which may regulate the mechanism of programmed cell death. We speculate that the apparent affinity of enediyne 2 for a key component of the apoptotic pathway enhances the ability of this pathway to prevent apoptosis. Enediyne 1, on the other hand, may have an affinity for the same component but acts to interfere with its function by generation of highly reactive free radicals. This hypothesis further suggests that affinity may be a principal determinant in generating the rearrangement reaction and that the stable enediynes may be molecular mimics of biomolecules which serve to regulate the progression of cell death pathways in Molt-4 cells. Further definition of the apparent agonist-antagonist relationship of stable and unstable enediynes will require the characterization of their target site interactions.

Understanding the mechanism by which enediyne 1 selectively kills human leukemic cells will also depend on isolation and characterization of cellular targets. We have observed however that various other cell lines which are moderately susceptible to enediyne 1 do not readily undergo apoptosis when exposed to toxic concentrations. The thousand fold greater susceptibility of the human leukemic Molt-4 line compared to all other cell lines tested may be a reflection of the propensity of human leukemic cells to undergo apoptotic death. The target of the synthetic enediynes in Molt-4 cells may help to define cellular junctions through which apoptotic cell death programs must pass. Conceivably, the synthetic enediynes could act by a mechanism from which a generalized strategy for the control of cell death programs in various cell types might emerge.

What is claimed is:

1. A method for inducing apoptosis within a leukocyte, the method employing the step of contacting the leukocyte with an unstable dynemicin-like enediyne for inducing apoptosis of the leukocyte, apoptosis of the leukocyte being induced by binding the unstable dynemicin-like enediyne to a proteinaceous material within the leukocyte and triggering a Bergman reaction, the unstable dynemicin-like enediyne including an enediyne susceptible to the Bergman reaction upon triggering, the unstable dynemicin-like enediyne including a trigger attached thereto for triggering the Bergman reaction within the unstable dynemicin-like enediyne, the trigger being activatable at intracellular alkaline pH, the unstable dynemicin-like enediyne having a binding specificity for a proteinaceous material within the leukocyte.

2. A method as described in claim 1 wherein the leukocyte is a molt-4 cell and the unstable dynemicin-like enediyne has the following structure:

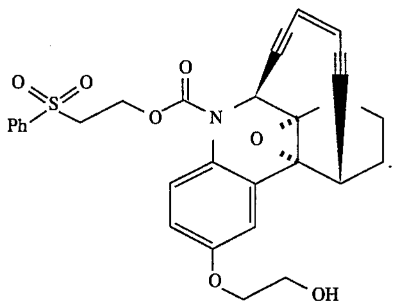

1

3. A method for inhibiting apoptosis within a leukocyte, the apoptosis being of a type that is inducible by an unstable dynemicin-like enediyne, the method employing the step of contacting the leukocyte with a stable dynemicin-like enediyne for inhibiting the apoptosis of the leukocyte, the apoptosis of the leukocyte being inhibited by binding the stable dynemicin-like enediyne to a proteinaceous material within the leukocyte, the stable dynemicin-like enediyne lacking a trigger and including an enediyne unsusceptible to the Bergman reaction at intracellular alkaline pH, the stable dynemicin-like enediyne having a binding specificity for a proteinaceous material within the leukocyte.

4. A method as described in claim 3 wherein the leukocyte is a molt-4 cell and the stable dynemicin-like enediyne has the following structure:

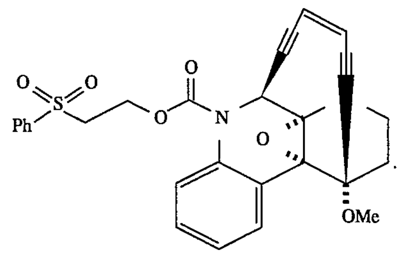

2

* * * * *